United States Patent [19]

Maurer et al.

[11] 4,155,998
[45] May 22, 1979

[54] ARTHROPODICIDALLY ACTIVE 1-PHENYL-1,6-DIHYDROPYRIDAZ-6-ON-3-YL(THIONO)-PHOSPHORIC (PHOSPHONIC) ACID ESTERS

[75] Inventors: Fritz Maurer, Wuppertal; Erich Klauke, Odenthal; Ingeborg Hammann, Cologne; Wolfgang Behrenz, Overath, all of Fed. Rep. of Germany

[73] Assignee: Bayer Aktiengesellschaft, Leverkusen, Fed. Rep. of Germany

[21] Appl. No.: 873,996

[22] Filed: Jan. 31, 1978

[30] Foreign Application Priority Data

Feb. 12, 1977 [DE] Fed. Rep. of Germany ....... 2705995

[51] Int. Cl.² ............................ C07F 9/65; A01N 9/36
[52] U.S. Cl. .................................. 424/200; 544/232; 544/240
[58] Field of Search .......................... 544/232; 424/200

[56] References Cited

U.S. PATENT DOCUMENTS 2,759,937  8/1956  Du Breuil .................... 260/250 A
4,013,657  3/1977  Hofer et al. ..................... 71/87

FOREIGN PATENT DOCUMENTS 844857  2/1977  Belgium.

Primary Examiner—Mark L. Berch
Attorney, Agent, or Firm—Sprung, Felfe, Horn, Lynch & Kramer

[57] ABSTRACT

1-Phenyl-1,6-dihydropyridaz-6-on-3-yl-(thiono)-phosphoric (phosphonic) acid esters of the formula

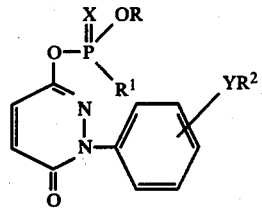

in which
R is alkyl,
$R^1$ is alkyl or alkoxy,
$R^2$ is halogenoalkyl, and
X and Y each independently is oxygen or sulphur,
which possess arthropodicidal properties.

10 Claims, No Drawings

ARTHROPODICIDALLY ACTIVE 1-PHENYL-1,6-DIHYDROPYRIDAZ-6-ON-3-YL-(THIONO)-PHOSPHORIC(PHOSPHONIC) ACID ESTERS

The present invention relates to and has for its objects the provision of particular new 1-phenyl-1,6-dihydropyridaz-6-on-3-yl-(thiono)-phosphoric (phosphonic) acid esters which possess arthropodicidal properties, active compositions in the form of mixtures of such compounds with solid and liquid dispersible carrier vehicles, and methods for producing such compounds and for using such compounds in a new way especially for combating pests, e.g. arthropods, with other and further objects becoming apparent from a study of the within specification and accompanying examples.

It is already known that certain pyridazinonethionophosphoric and -phosphonic acid esters, for example O,O-diethyl-O-[1-phenyl-1,6-dihydropyridaz-6-on-3-yl]-thionophosphoric acid ester and O-ethyl-O-[1-phenyl-1,6-dihydropyridaz-6-on-3-yl]-thionoethanephosphonic acid ester, are distinguished by an insecticidal and acaricidal activity (see U.S. Pat. No. 2,759,937 and Belgian Pat. No. 844,857).

The present invention now provides, as new compounds, the pyridazinone(thiono)-phosphoric(phosphonic) acid esters of the general formula

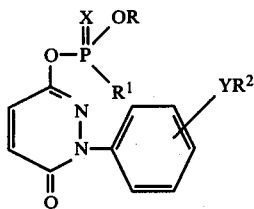

in which
R represents alkyl,
$R^1$ represents alkyl or alkoxy,
$R^2$ represents halogenalkyl and
X and Y, which may be identical or different, each represents oxygen or sulfur.

Preferably, R represents straight-chain or branched alkyl with 1 to 6 (especially 1 to 4) carbon atoms, $R^1$ represents straight-chain or branched alkyl or alkoxy each with 1 to 5 (especially 1 to 3) carbon atoms, $R^2$ represents straight-chain or branched halogenalkyl with 1 to 4 (especially 1 or 2) carbon atoms (the halogen therein preferably being fluorine or fluorine and chlorine), X represents sulphur and Y represents oxygen or sulphur.

Surprisingly, the pyridazinone(thiono)-phosphoric (phosphonic) acid esters according to the invention exhibit a better insecticidal and acaricidal action than the corresponding previously known pyridazinonethiono-phosphoric and -phosphonic acid esters of analogous structure and of the same type of action. The products according to the present invention thus represent a genuine enrichment of the art.

The invention also provides a process for the preparation of a pyridazinone(thiono)-phosphoric(phosphonic) acid ester of the formula (I) in which a (thiono)phosphoric (phosphonic) acid ester halide of the general formula

in which
R, $R^1$ and X have the above-mentioned meanings and
Hal represents halogen, preferably chlorine, is reacted, if appropriate in the presence of a solvent of diluent, with a 3-hydroxy-1,6-dihydropyridazinone of the general formula

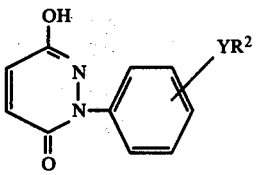

in which
$R^2$ and Y have the above-mentioned meanings, the latter being employed in the form of an alkali metal salt, alkaline earth metal salt of ammonium salt or as such in the presence of an acid acceptor.

If, for example, O-sec.-butyl-ethanephosphonic acid ester chloride and 1-[3-(1,1,2,2-tetrafluoroethylthiophenyl)]-1,6-dihydro-3-hydroxy-pyridazin-6-one are used as starting materials, the course of the reaction can be represented by the following equation:

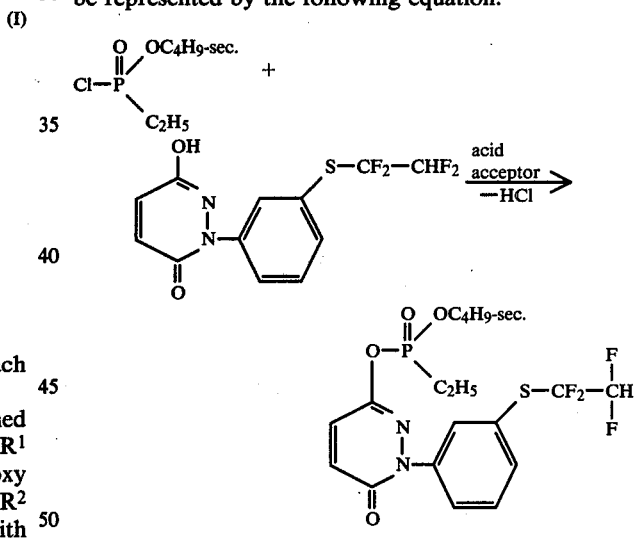

The (thiono)phosphoric(phosphonic) acid ester halides (II) to be used as starting materials are known. The following may be mentioned individually as examples thereof: O,O-dimethyl-, O,O-diethyl-, O,O-di-n-propyl-, O,O-di-isopropyl-, O-methyl-O-ethyl-, O-methyl-O-n-propyl-, O-methyl-O-iso-propyl-, O-methyl-O-n-butyl-, O-methyl-O-isobutyl-, O-methyl-O-sec.-butyl-, O-ethyl-O-n-propyl-, O-ethyl-O-iso-propyl-, O-ethyl-O-n-butyl-, O-ethyl-O-sec.-butyl-, O-ethyl-O-iso-butyl-, O-n-propyl-O-butyl- and O-iso-propyl-O-butyl-phosphoric acid diester chloride and the corresponding thiono analogues and O-methyl-, O-ethyl-, O-n-propyl-, O-iso-propyl-, O-n-butyl-, O-iso-butyl- and O-sec.-butyl-methane-, -ethane-, -n-propane-and -iso-propane-phosphonic acid ester chloride and the corresponding thiono analogues.

The following may be mentioned as examples of the 3-hydroxy-1,6-dihydro-pyridazinones (III) are to be used as starting materials: 1-(4-trifluoromethoxyphenyl)-, 1-(4-trifluoromethylthiophenyl)-, 1-(3-trifluoromethoxyphenyl)-, 1-(3-trifluoromethylthiophenyl)-, 1-(4-difluoromethoxyphenyl)-, 1-(4-difluoromethylthiophenyl)-, 1-(3-difluoromethoxyphenyl)-, 1-(3-difluoromethylthiophenyl)-, 1-[4-(1,1,2,2-tetrafluoroethoxy)-phenyl]-, 1-[4-(1,1,2,2-tetrafluoroethylthio)-phenyl]-, 1-[3-(1,1,2,2-tetrafluoroethoxy)-phenyl]-, 1-[3-(1,1,2,2-tetrafluoroethylthio)-phenyl]-, 1-[4-(1,1,2-trifluoro-2-chloroethoxy)-phenyl]-, 1-[4-(1,1,2-trifluoro-2-chloroethylthio)-phenyl]-, 1-[3-(1,1,2-trifluoro-2-chloroethoxy)-phenyl]- and 1-[3-(1,1,2-trifluoro-2-chloroethylthio)-phenyl]-1,6-dihydro-3-hydroxypyridazin-6-one.

The process for the preparation of the compounds according to the invention is preferably carried out in the presence of a suitable solvent or diluent. Virtually all inert organic solvents can be used for this purpose, especially aliphatic and aromatic, optionally chlorinated hydrocarbons, such as benzene, toluene, xylene, benzine, methylene chloride, chloroform, carbon tetrachloride and chlorobenzene; esthers, for example diethyl ether, dibutyl ether and dioxane; ketones, for example acetone, methyl ethyl ketone, methyl isopropyl ketone and methyl isobutyl ketone; and nitriles, such as acetonitrile and propionitrile.

All customary acid-binding agents can be used as acid acceptors. Alkali metal carbonates and alkali metal alcoholates, such as sodium carbonate and potassium carbonate, sodium methylate and ethylate and potassium methylate, ethylate or tert.-butylate have proved particularly suitable, as have aliphatic, aromatic or heterocyclic amines, for example triethylamine, trimethylamine, dimethylaniline, dimethylbenzylamine and pyridine.

The reaction temperature can be varied within a substantial range. In general, the reaction is carried out at from 0° to 120° C., preferably at from 15° to 60° C.

In general, the reaction is allowed to take place under normal pressure.

To carry out the process, the starting components are preferably employed in stoichiometric amounts. An excess of one or other of the components produces no significant advantages. In general, the reactants are brought together in one of the stated solvents and in most cases stirred at an elevated temperature for one or more hours to complete the reaction. The reaction solution is then cooled and extracted by shaking with water, and the organic phase is worked up in the usual manner by drying, and distilling off the solvent.

The new compounds are mostly obtained in the form of oils which in part cannot be distilled without decomposition, but are freed from the last volatile constituents by so-called "slight distillation", that is to say by prolonged heating under reduced pressure to moderately elevated temperatures, and are purified in this way. They are characterized by the refractive index. Some compounds are obtained in a crystalline form and are characterized by their melting points.

The 3-hydroxy-1,6-dihydropyridazinones of the formula (III), which have not previously been described in the literature, can be prepared in accordance with processes which are in themselves known. For example, it is possible to diazotize the corresponding halogenalkoxyanilines or halogenalkylthioanilines of the general formula

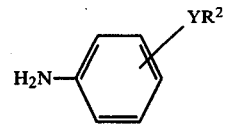

in which

Y and $R^2$ have the above-mentioned meanings, convert the diazonium compound to the hydrazine by adding reducing agents such as, for example, tin(II) chloride, and react the hydrazine with maleic anhydride to give the desired product.

As already mentioned, the compounds according to the present invention are distinguished by an excellent insecticidal and acaricidal activity. They are therefore active against plant pests, pests harmful to health and pests of stored products and combine a low phytotoxicity with a good action against sucking and biting insects and against mites.

For this reason, the compounds according to the invention can be employed successfully as pesticides in plant protection and in the hygiene field and the field of protection of stored products.

The active compounds are well tolerated by plants, have a favorable level of toxicity to warm-blooded animals, and can be used for combating arthropod pests, especially insects and acarids, which are encountered in agriculture, in forestry, in the protection of stored products and of materials, and in the hygiene field. They are active against normally sensitive and resistant species and against all or some stages of development. The abovementioned pests include:

from the class of the Isopoda, for example *Oniscus asellus, Armadillidum vulgare* and *Porcellio scaber;* from the class of the Diplopoda, for example *Blaniulus guttulatus;* from the class of the Chilopoda, for example *Geophilus carpophagus* and *Scutigera* spec.;

from the class of the Symphyla, for example *Scutigerella immaculata;* from the order of the Thysanura, for example *Lepisma saccharina;* from the order of the Collembola, for example *Onychiurus armatus;* from the order of the Orthoptera, for example *Blatta orientalis, Periplaneta americana, Leucophaea maderae, Blattella germanica, Acheta domesticus,* Gryllotalpa spp., *Locusta migratoria migratorioides, Melanoplus differentialis* and *Schistocerca gregaria;* from the order of the Dermaptera, for example *Forficula auricularia;* from the order of the Isoptera, for example Reticulitermes spp.;

from the order of the Anoplura, for example *Phylloxera vastatrix,* Pemphigus spp., *Pediculus humanus corporis,* Haematopinus spp. and Linognathus spp.;

from the order of the Mallophaga, for example Trichodectes spp. and Damalinea spp.;

from the order of the Thysanoptera, for example *Hercinothrips femoralis* and *Thrips tabaci;* from the order of the Heteroptera, for example Eurygaster spp., *Dysdercus intermedius, Piesma quadrata, Cimex lectularius, Rhodnius prolixus* and Triatoma spp.;

from the order of the Homoptera, for example *Aleurodes brassicae, Bemisia tabaci, Trialeurodes vaporariorum, Aphis gossypii, Brevicoryne brassicae, Cryptomyzus ribis, Doralis fabae, Doralis pomi, Eriosoma lanigerum,*

*Hyalopterus arundinis, Macrosiphum avenae,* Myzus spp.; *Phorodon humuli, Rhopalosiphum padi,* Empoasca spp.; *Euscelis bilobatus, Nephotettix cincticeps, Lecanium corni, Saissetia oleae, Laodelphax striatellus, Nilaparvata lugens, Aonidiella aurantii, Aspidiotus hederae,* Pseudococcus spp. and Psylla spp.;

from the order of the Lepidoptera, for example *Pectinophora gossypiella, Bupalus piniarius, Cheimatobia brumata, Lithocolletis blancardella, Hyponomeuta padella, Plutella maculipennis, Malacosoma neustria, Euproctis chrysorrhoea,* Lymantria spp., *Bucculatrix thurberiella, Phyllocnistis citrella,* Agrotis spp., Euxoa spp., Feltia spp., *Earias insulana,* Heliothis spp., *Laphygma exigua, Mamestra brassicae, Panolis flammea, Prodenia litura,* Spodoptera spp., *Trichoplusia ni, Carpocapsa pomonella,* Pieris spp., Chilo spp., *Pyrausta nubilalis, Ephestia kuehniella, Galleria mellonella, Cacoecia podana, Capua reticulana, Choristoneura fumiferana, Clysia ambiguella, Homona magnanima* and *Tortrix viridana;* from the order of the Coleoptera, for example *Anobium punctatum, Rhizopertha dominica, Bruchidius obtectus, Acanthoscelides obtectus, Hylotrupes bajulus, Agelastica alni, Leptinotarsa decemlineata, Phaedon cochleariae,* Diabrotica spp., *Psylliodes chrysocephala, Epilachna varivestis,* Atomaria spp., *Oryzaephilus surinamensis,* Anthonomus spp., Sitophilus spp., *Otiorrhynchus sulcatus, Cosmopolites sordidus, Ceuthorrhynchus assimilis, Hypera postica,* Dermestes spp., Trogoderma spp., Anthrenus spp., Attagenus spp., Lyctus spp., *Meligethes aeneus,* Ptinus spp., *Niptus hololeucus, Gibbium psylloides,* Tribolium spp., *Tenebrio molitor,* Agriotes spp., Conoderus spp., *Melolontha melolontha, Amphimallon solstitialis* and *Costelytra zealandica;* from the order of the Hymenoptera, for example Diprion spp., Hoplocampa spp., Lasius spp., *Monomorium pharaonis* and Vespa spp.;

from the order of the Diptera, for example Aedes spp., Anopheles spp., Culex spp., *Drosophila melanogaster,* Musca spp., Fannia spp., *Calliphora erythrocephala,* Lucilia spp., Chrysomyia spp., Cuterebra spp., Gastrophilus spp., Hyppobosca spp., Stomoxys spp., Oestrus spp., Hypoderma spp., Tabanus spp., Tannia spp., *Bibo hortulanus, Oscinella frit,* Phorbia spp., *Pegomyia hyoscyami, Ceratitis capitata, Dacus oleae* and *Tipula paludosa;* from the order of the Siphonaptera, for example *Xenopsylla cheopis* Ceratophyllus spp.;

from the class of the Arachnida, for example *Scorpio maurus* and *Latrodectus mactans;* from the order of the Acarina, for example *Acarus siro,* Argas spp., Ornithodoros spp., *Dermanyssus gallinae, Eriophyes ribis, Phyllocoptruta oleivora,* Boophilus spp., Rhipicephalus spp., Amblyomma spp., Hyalomma spp., Ixodes spp., Psoroptes spp., Chorioptes spp., Sarcoptes spp., Tarsonemus spp., *Bryobia praetiosa,* Panonychus spp. and Tetranychus spp. Trichodorus spp.

When used against hygiene pests and pests of stored products, the active compounds are distinguished by an excellent residual activity on wood and clay as well as a good stability to alkali on limed substrates.

The active compounds according to the instant invention can be utilized, if desired, in the form of the usual formulations or compositions with conventional inert (i.e. plant compatible or herbicidally inert) pesticide diluents or extenders, i.e. diluents, carriers or extenders of the type usable in conventional pesticide formulations or compositions, e.g. conventional pesticide dispersible carrier vehicles such as gases, solutions, emulsions, wettable powders suspensions, powders, dusting agents, foams, pastes, soluble powders, granules, aerosols, suspension-emulsion concentrates, seed-treatment powders, natural and synthetic materials impregnated with active compound, very fine capsules in polymeric substances and in coating compositions, for use on seed, and formulations used with burning equipment, such as fumigating cartridges, fumigating cans, fumigating coils and the like, as well as ULV cold mist and warm mist formulations.

These are prepared in known manner, for instance by extending the active compounds with conventional perticide dispersible liquid diluent carriers and/or dispersible solid carriers optionally with the use of carrier vehicle assistants, e.g. conventional pesticide surface-active agents, including emulsifying agents and/or dispersing agents, whereby, for example, in the case where water is used as diluent, organic solvents may be added as auxiliary solvents. The following may be chiefly considered for use as conventional carrier vehicles for this purpose: aerosol propellants which are gaseous at normal temperatures and pressures, such as halogenated hydrocarbons, e.g. dichlorodifluoromethane and trichloromethane, as well as butane, propane, nitrogen and carbon dioxide; inert dispersible liquid diluent carriers, including inert organic solvents, such as aromatic hydrocarbons (e.g. benzene, toluene, xylene, alkyl naphthalenes, etc.), halogenated, especially chlorinated, aromatic hydrocarbons (e.g. chlorobenzenes, etc.), cycloalkanes, (e.g. cyclohexane, etc.), paraffins (e.g. petroleum or mineral oil fractions), chlorinated aliphatic hydrocarbons (e.g. methylene chloride, chloroethylenes, etc.), alcohols (e.g. methanol, ethanol, propanol, butanol, glycol, etc.) as well as ethers and esters thereof (e.g. glycol monomethyl ether, etc.), amines (e.g. ethanolamine, etc.), amides (e.g. dimethyl formamide, etc.), sulfoxides (e.g. dimethyl sulfoxide, etc.), acetonitrile, ketones (e.g. acetone, methyl ethyl ketone, methyl isobutyl ketone, cyclohexanone, etc.), and/or water; as solid carriers, ground natural minerals, such as kaolins, clays, talc, chalk, quartz, attapulgite, montmorillonite or diatomaceous earth, and ground synthetic minerals, such as highly-dispersed silicic acid, alumina and silicates; as solid carriers for granules; crushed and fractionated natural rocks such as calcite, marble, pumice, sepiolite and dolomite, as well as synthetic granules of inorganic and organic meals, and granules of organic material such as sawdust, coconut shells, corn cobs and tobacco stalks; whereas the following may be chiefly considered for use as conventional carrier vehicle assistants, e.g. surface-active agents, for this purpose: emulsifying agents, such as non-ionic and/or anionic emulsifying agents (e.g. polyethylene oxide esters of fatty acids, polyethylene oxide ethers of fatty alcohols, alkyl sulfates, alkyl sulfonates, aryl sulfonates, albumin hydrolyzates, etc., and especially alkyl arylpolyglycol ethers, magnesium stearate, sodium oleate, etc.); and/or dispersing agents, such as lignin, sulfite waste liquors, methyl cellulose, etc.

Adhesives such as carboxymethylcellulose and natural and synthetic polymers in the form of powders, granules or latices, such as gum arabic, polyvinyl alcohol and polyvinyl acetate, can be used in the formulations.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

Such active compounds may be employed alone or in the form of mixtures with one another and/or with such solid and/or liquid dispersible carrier vehicles and/or with other known compatible active agents, especially plant protection agents, such as other arthropodicides, or nematicides, fungicides, bactericides, rodenticides, herbicides, fertilizers, growth-regulating agents, etc., if desired, or in the form of particular dosage preparations for specific application made therefrom, such as solutions, emulsions, suspensions, powders, pastes, and granules which are thus ready for use.

As concerns commercially marketed preparations, these generally contemplate carrier composition mixtures in which the active compound is present in an amount substantially between about 0.1–95% by weight, and preferably 0.5–90% by weight, of the mixture, whereas carrier composition mixtures suitable for direct application or field application generally contemplate those in which the active compound is present in an amount substantially between about 0.0000001–100, preferably 0.01–10%, by weight of the mixture. Thus, the present invention contemplates overall compositions which comprise mixtures of a conventional dispersible carrier such as (1) a dispersible inert finely divided carrier solid, and/or (2) a dispersible carrier liquid such as an inert organic solvent and/or water, preferably including a surface-active effective amount of a carrier vehicle assistant, e.g. a surface-active agent, such as an emulsifying agent and/or a dispersing agent, and an amount of the active compound which is effective for the purpose in question and which is generally between about 0.0001–95%, and preferably 0.01–95%, by weight of the mixture.

The active compounds can also be used in accordance with the well known ultra-low-volume process with good success, i.e. by applying such compound if normally a liquid, or by applying a liquid composition containing the same, via very effective atomizing equipment, in finely divided form, e.g. average particle diameter of from 50–100 microns, or even less, i.e. mist form, for example by airplane crop spraying techniques. Only up to at most about a few liters/hectare are needed, and often amounts only up to about 15 to 1000 g/hectare, preferably 40 to 600 g/hectare, are sufficient. In this process it is possible to use highly concentrated liquid compositions with said liquid carrier vehicles containing from about 20 to about 95% by weight of the active compound or even the 100% active substance alone, e.g. about 20–100% by weight of the active compound.

Furthermore, the present invention contemplates methods of selectively killing, combating or controlling pests, e.g. arthropods, which comprises applying to at least one of correspondingly (a) such arthropods, and (b) the corresponding habitat thereof, i.e. the locus to be protected, e.g. to a growing crop, to an area where a crop is to be grown or to a domestic animal, a correspondingly combative or toxic amount, i.e. an arthropodicidally effective amount, of the particular active compound of the invention alone or together with a carrier vehicle as noted above. The instant formulations or compositions are applied in the usual manner, for instance by spraying, atomizing, vaporizing, scattering, dusting, watering, squirting, sprinkling, pouring, fumigating, dry dressing, moist dressing, wet dressing, slurry dressing, encrusting, and the like.

It will be realized, of course, that the concentration of the particular active compound utilized in admixture with the carrier vehicle will depend upon the intended application. Therefore, in special cases it is possible to go above or below the aforementioned concentration ranges.

The preparation of the new compounds of the present invention is illustrated, without limitation, by the following examples:

EXAMPLE 1

(a) The substituted pyridazinones of the formula (III), to be used as starting materials for the preparation of the compounds of the formula (I), could be prepared, for example, as follows:

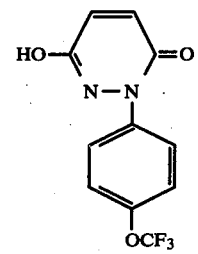

A solution of 68.3 g of sodium nitrite in 135 ml of water was added dropwise, at 0°–5° C., to a solution of 133 g (0.75 mol) of 4-trifluoromethoxyaniline in 300 ml of concentrated hydrochloric acid and 300 ml of water. After the end of the addition, the reaction mixture was allowed to run, at 5°–10° C., into a solution of 450 g of tin chloride hydrate in 450 ml of hydrochloric acid. After half an hour the salt which had precipitated was filtered off and dissolved in 900 ml of hot water, and the solution was filtered. 73.5 g (0.75 mol) of maleic anhydride were then added to the filtrate at 95°–100° C. and the mixture was stirred for a further hour at 100° C. The product which had precipitated was filtered off at 80° C., rinsed with warm water and then dissolved in dilute sodium hydroxide solution. The filtered solution was acidified with hydrochloric acid and the product which had crystallized out was then filtered off and rinsed with water. 99 g (49% of theory) of 1-(4-trifluoromethoxyphenyl)-3-hydroxy-1,6-dihydropyridazin-6-one were thus obtained in the form of a beige powder of melting point 243° C.

The following compounds of the formula

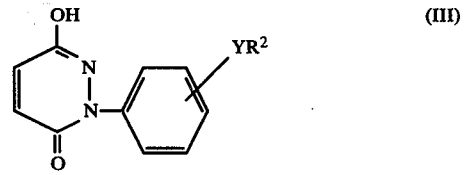

could be prepared analogously:

TABLE 1

| $R^2$ | Y | Position of the substituent $YR^2$ | Yield (% of theory) | Melting point, °C. |
| --- | --- | --- | --- | --- |
| $CF_3$ | 0 | 3 | 15 | 185 |
| $CF_3$ | S | 4 | 32 | 231 |
| $CHF_2$ | 0 | 4 | 34 | 241 |

TABLE 1-continued

| R² | Y | Position of the substituent YR² | Yield (% of theory) | Melting point, °C. |
|---|---|---|---|---|
| CF₂—CHF—Cl | 0 | 4 | 27 | 227 |
| CHF₂ | 0 | 3 | 31 | 161 |
| CF₂—CHF₂ | 0 | 4 | 59 | 243 |
| CHF₂ | S | 4 | 27 | 217 |

(b)

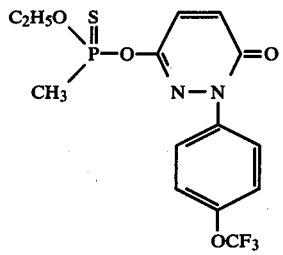

(1)

A mixture of 27.2 g (0.1 mol) of 1-(4-trifluoromethoxyphenyl)-3-hydroxy-1,6-dihydropyridazin-6-one, 20.7 g (0.15 mol) of potassium carbonate, 300 ml of methyl isobutyl ketone and 15.9 g (0.1 mol) of O-ethylmethanethionophosphonic acid ester chloride was stirred for 3 hours at 45° C. The reaction mixture was then cooled to room temperature and was shaken twice with 300 ml of water at a time. The organic phase was separated off, dried over sodium sulphate and freed from the solvent in vacuo. The residue was subjected to slight distillation. 29.8 g (76% of theory) of O-ethyl-O-[1-(4-trifluoromethoxyphenyl)-1,6-dihydropyridaz-6-on-3-yl]-methanethionophosphonic acid ester were thus obtained in the form of a brown oil having a refractive index $n_D^{20}$ of 1.5402.

The following compounds of the formula

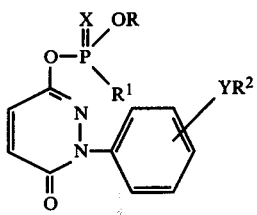

(I)

could be prepared analogously:

The activity of the compounds of this invention is illustrated by the following biotest examples wherein the compounds according to the present invention are each identified by the number (given in brackets) from the preparative example hereinabove.

The known comparison compounds are identified as follows:

(A) = 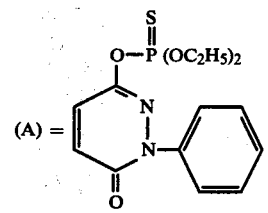

(B) = 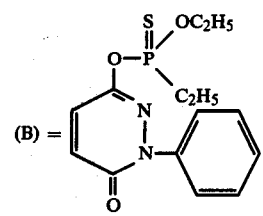

EXAMPLE 2

Plutella test
Solvent: 3 parts by weight of acetone
Emulsifier: 1 part by weight of alkylaryl polyglycol ether To produce a suitable preparation of active compound, 1 part by weight of the active compound was mixed with the stated amount of solvent containing the stated amount of emulsifier and the concentrate was diluted with water to the desired concentration.

Cabbage leaves (Brassica oleracea) were sprayed with the preparation of the active compound until dew moist and were then infested with caterpillars of the diamondback moth (Plutella maculipennis).

After the specified periods of time, the degree of destruction was determined as a percentage: 100% meant that all of the caterpillars were killed whereas 0% meant that none of the caterpillars were killed.

TABLE 2

| Compound No. | R | R¹ | R² | X | Y | Position of the substituent YR² | Yield (% of theory) | Physical data (refractive index; melting point, °C.) |
|---|---|---|---|---|---|---|---|---|
| 2 | C₂H₅ | C₂H₅O | CF₃ | S | 0 | 4 | 76 | $n_D^{20}$:1.5251 |
| 3 | C₂H₅ | C₂H₅ | CF₃ | S | 0 | 4 | 79 | $n_D^{20}$:1.5357 |
| 4 | iso-C₃H₇ | CH₃ | CF₃ | S | 0 | 4 | 79 | $n_D^{20}$:1.5340 |
| 5 | C₂H₅ | CH₃ | CHF₂ | S | 0 | 4 | 76 | $n_D^{22}$:1.5642 |
| 6 | C₂H₅ | CH₃ | CF₂—CHFCl | S | 0 | 4 | 55 | $n_D^{22}$:1.5458 |
| 7 | iso-C₃H₇ | CH₃ | CF₂—CHFCl | S | 0 | 4 | 53 | $n_D^{22}$:1.5402 |
| 8 | C₂H₅ | CH₃ | CF₃ | S | 0 | 3 | 58 | $n_D^{22}$:1.5328 |
| 9 | iso-C₃H₇ | CH₃ | CHF₂ | S | 0 | 4 | 66 | $n_D^{22}$:1.5527 |
| 10 | C₂H₅ | C₂H₅ | CHF₂ | S | 0 | 4 | 66 | $n_D^{22}$:1.5575 |
| 11 | C₂H₅ | CH₃ | CF₃ | S | S | 4 | 47 | $n_D^{22}$:1.5617 |
| 12 | C₂H₅ | CH₃ | CHF₂ | S | 0 | 3 | 59 | $n_D^{21}$:1.5638 |
| 13 | C₂H₅ | CH₃ | CF₂—CHF₂ | S | 0 | 4 | 50 | $n_D^{21}$:1.5330 |
| 14 | iso-C₃H₇ | CH₃ | CHF₂ | S | 0 | 3 | 51 | $n_D^{21}$:1.5568 |
| 15 | iso-C₃H₇ | CH₃ | CF₂—CHF₂ | S | 0 | 4 | 48 | $n_D^{22}$:1.5259 |
| 16 | C₂H₅ | C₂H₅ | CF₂—CHF₂ | S | 0 | 4 | 55 | $n_D^{22}$:1.5300 |
| 17 | C₂H₅ | C₂H₅O | CF₂—CHF₂ | S | 0 | 4 | 60 | $n_D^{22}$:1.5198 |
| 18 | iso-C₃H₇ | CH₃ | CF₃ | S | S | 4 | 31 | 87 |
| 19 | C₂H₅ | C₂H₅ | CF₃ | S | S | 4 | 50 | $n_D^{22}$:1.5612 |
| 20 | C₂H₅ | C₂H₅O | CF₃ | S | S | 4 | 48 | $n_D^{22}$:1.5512 |

The active compounds, the concentrations of the active compounds, the evaluation times and the results can be seen from the following table:

Table 3

| Active compounds | (Insects which damage plants) Plutella test | |
|---|---|---|
| | Active compound concentration in % | Degree of destruction in % after 3 days |
| (A) | 0.01 | 100 |
| | 0.001 | 0 |
| (2) | 0.01 | 100 |
| | 0.001 | 100 |
| (8) | 0.01 | 100 |
| | 0.001 | 90 |
| (3) | 0.01 | 100 |
| | 0.001 | 100 |
| (16) | 0.01 | 100 |
| | 0.001 | 90 |
| (19) | 0.01 | 100 |
| | 0.001 | 100 |
| (11) | 0.01 | 100 |
| | 0.001 | 100 |

EXAMPLE 3

Tetranychus test (resistant)
Solvent: 3 parts by weight of acetone
Emulsifier: 1 part by weight of alkylaryl polyglycol ether To produce a suitable preparation of active compound, 1 part by weight of the active compound was mixed with the stated amount of solvent and the stated amount of emulsifier and the concentrate was diluted with water to the desired concentration.

Bean plants (*Phaseolus vulgaris*) which were heavily infested with the two-spotted spider mite (*Tetranychus urticae*) in all stages of development were sprayed with the preparation of the active compound until dripping wet.

After the specified periods of time, the degree of distruction was determined as a percentage: 100% meant that all of the spider mites were killed whereas 0% meant that none of the spider mites were killed.

The active compounds, the concentrations of the active compounds, the evaluation times and the results can be seen from the following table:

Table 4

| Active compounds | (Mites which damage plants) Tetranychus test | |
|---|---|---|
| | Active compound concentration in % | Degree of destruction in % after 2 days |
| (A) | 0.1 | 100 |
| | 0.01 | 0 |
| (3) | 0.1 | 100 |
| | 0.01 | 100 |
| (1) | 0.1 | 100 |
| | 0.01 | 100 |
| (8) | 0.1 | 100 |
| | 0.01 | 100 |
| (5) | 0.1 | 100 |
| | 0.01 | 100 |
| (11) | 0.1 | 100 |
| | 0.01 | 100 |
| (4) | 0.1 | 100 |
| | 0.01 | 100 |
| (18) | 0.1 | 100 |
| | 0.01 | 100 |
| (9) | 0.1 | 100 |
| | 0.01 | 100 |
| (15) | 0.1 | 100 |

Table 4-continued

| Active compounds | (Mites which damage plants) Tetranychus test | |
|---|---|---|
| | Active compound concentration in % | Degree of destruction in % after 2 days |
| | 0.01 | 100 |

EXAMPLE 4

$LT_{100}$ test for Diptera
Test insects *Aedes aegypti*
Solvent: Acetone

The active compound was dissolved in the solvent at a rate of 2 g per liter. The solution so obtained was diluted with further solvent to the desired lower concentrations.

2.5 ml of the solution of active compound were pipetted into a Petri dish. On the bottom of the Petri dish there was a filter paper with a diameter of about 9.5 cm. The Petri dish remained uncovered until the solvent had completely evaporated. The amount of active compound per square meter of filter paper varied with the concentration of the solution of active compound. About 25 test insects were then placed in the Petri dish and it was covered with a glass lid.

The condition of the test insects was continuously observed. The time which was necessary for 100% destruction was determined.

The active compounds, the concentrations of the active compounds and the times at which there was 100% destruction can be seen from the following table:

Table 5

| Active compounds | ($LT_{100}$ test for Diptera) *Aedes aegypti* | |
|---|---|---|
| | Active compound concentration of the solution in % | $LT_{100}$ |
| (A) | 0.02 | 3 hrs = 0% |
| (B) | 0.02 | 3 hrs = 0% |
| (6) | 0.02 | 120' |
| (8) | 0.02 | 3 hrs |
| (11) | 0.02 | 120' |
| (12) | 0.02 | 3 hrs |
| (13) | 0.02 | 120' |
| (17) | 0.02 | 3 hrs = 60% |
| (20) | 0.02 | 120' |

It will be appreciated that the instant specification and examples are set forth by way of illustration and not limitation, and that various modifications and changes may be made without departing from the spirit and scope of the present invention.

What is claimed is:

1. A phenyl-1,6-dihydropyridaz-6-on-3-yl-(thiono)-phosphoric(phosphonic) acid ester of the formula

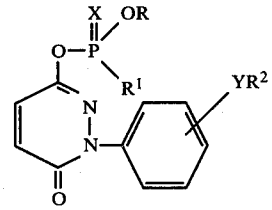

in which
R is alkyl with 1 to 6 carbon atoms, $R^1$ is alkyl or alkoxy with 1 to 5 carbon atoms,
$R^2$ is halogenalkyl with 1 to 4 carbon atoms, and
X and Y each independently is oxygen or sulphur.

2. A compound according to claim 1, in which X is sulphur.

3. A compound according to claim 1, wherein such compound is O-ethyl-O-[1-(4-trifluoromethoxyphenyl)-1,6-dihydropyridaz-6-on-3-yl]-ethanethionophosphonic acid ester of the formula

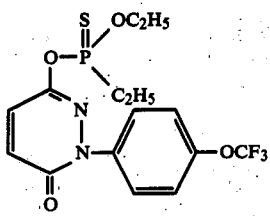

4. A compound according to claim 1, wherein such compound is O-isopropyl-O-[1-(4-trifluoromethoxyphenyl)-6-on-yl]-methanethionophosphonic acid ester of the formula

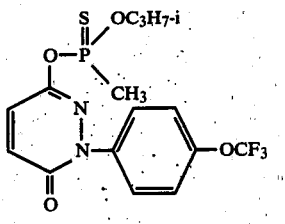

5. A compound according to claim 1, wherein such compound is O-ethyl-O-[1-(3-trifluoromethoxyphenyl)-1,6-dihydropyridaz-6-on-3-yl]-methanethionophosphonic acid ester of the formula

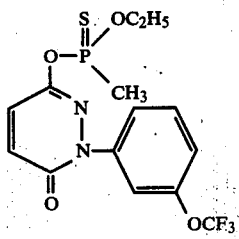

6. A compound according to claim 1, wherein such compound is O-isopropyl-O-[1-(4-difluoromethoxyphenyl)-1,6-dihydropyridaz-6-on-3-yl]-methanethionophosphonic acid ester of the formula

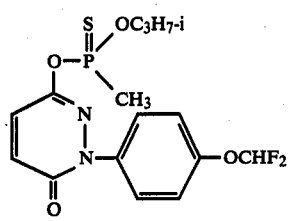

7. A compound according to claim 1, wherein such compound is O-ethyl-O-[1-(4-trifluoromethylthiophenyl)-1,6-dihydropyridaz-6-on-3-yl]-methanethionophosphonic acid ester of the formula

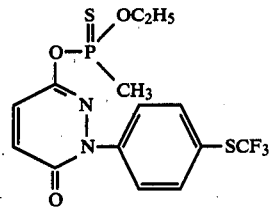

8. An arthropodicidal composition containing as active ingredient an arthropodicidally effective amount of a compound according to claim 1 in admixture with a diluent.

9. A method of combating insects and acarids which comprises applying to the insects, acarids, or to a habitat thereof, an insecticidally or acaricidally effective amount of a compound according to claim 1.

10. The method according to claim 9 in which said compound is

O-ethyl-O-[1-(4-trifluoromethoxyphenyl)-1,6-dihydropyridaz-6-on-3-yl]-ethane thionophosphonic acid ester, O-isopropyl-O-[1-(4-trifluoromethoxyphenyl)-1,6-dihydropyridaz-6-on-3-yl]-methanethionophosphonic acid ester, O-ethyl-O-[1-(3-trifluoromethoxyphenyl)-1,6-dihydropyridaz-6-on-3-yl]-methanethionophosphonic acid ester, O-isopropyl-O-[1-(4-difluoromethoxyphenyl)-1,6-dihydropyridaz-6-on-3-yl]-methanethionophosphonic acid ester, or O-ethyl-O-[1-(4-trifluoromethylthiophenyl)-1,6-dihydropyridaz-6-on-3-yl]-methanethionophsophonic acid ester.

* * * * *